United States Patent [19]

Bod et al.

[11] Patent Number: 4,835,281
[45] Date of Patent: May 30, 1989

[54] PROCESS FOR THE PREPARATION OF N-SULFAMYL-3-(2-GUANIDINO-THIAZOL-4-METHYLTHIO)-PROPIONAMIDINE

[75] Inventors: Péter Bod, Gyömrő; Kálmán Harsányi, Budapest; Éva Ágai neé Csongor, Budapest; Erik Bogsch, Budapest; Éva Fekecs, Budapest; Ferenc Trischler, Budapest; György Domány, Budapest; István Szabadkai, Budapest; Bëla Hegedüs, Budapest, all of Hungary

[73] Assignee: Richter Gedeon Vegyeszeti Gyar Rt., Budapest, Hungary

[21] Appl. No.: 77,095

[22] Filed: Jul. 23, 1987

Related U.S. Application Data

[63] Continuation-in-part of Ser. No. 905,835, Sep. 10, 1986, abandoned.

[30] Foreign Application Priority Data

Sep. 11, 1985 [HU] Hungary ............... 3424/85

[51] Int. Cl.$^4$ ........................... C07D 277/42
[52] U.S. Cl. ................................... 548/197
[58] Field of Search .......................... 548/197

[56] References Cited

U.S. PATENT DOCUMENTS

| 4,283,408 | 8/1981 | Hirata | 548/193 |
| 4,496,737 | 1/1985 | Hoffman | 548/193 |
| 4,731,479 | 3/1988 | Bod et al. | 564/79 |

FOREIGN PATENT DOCUMENTS

| 905409 | 12/1986 | Belgium | 546/197 |
| 0087274 | 8/1983 | European Pat. Off. | 546/197 |
| 2180237 | 3/1987 | United Kingdom | 548/197 |

*Primary Examiner*—Robert Gerstl
*Attorney, Agent, or Firm*—Herbert Dubno; Jonathan Myers

[57] ABSTRACT

The invention relates to a new process for the preparation of N-sulfamyl-3-(2-guanidinothiazol-4-yl-methylthio)-propionitrile (famotidine) of the formula (I)

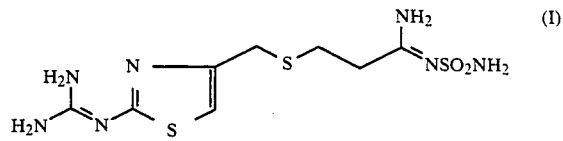

by S-alkylation of 2-guanidino-thiazol-4-yl-methane-thiol obtained from S-(2-guanidino-thiazol-4-yl-methyl)-isothiourea dihydrochloride of the formula (III)

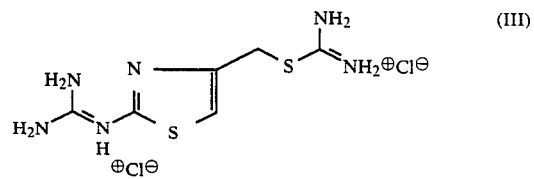

by in situ treatment with a base, which comprises carrying out S-alkylation with a N-sulfamyl-3-halopropionamidine of the formula (II)

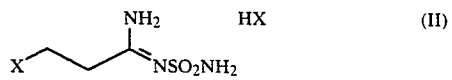

wherein X stands for halogen.

6 Claims, No Drawings

PROCESS FOR THE PREPARATION OF N-SULFAMYL-3-(2-GUANIDINO-THIAZOL-4-METHYLTHIO)-PROPIONAMIDINE

CROSS REFERENCE TO RELATED APPLICATION

This application is a continuation-in-part of Ser. No. 905,835 filed Sept. 10, 1986 now abandoned.

The invention relates to a new process for the preparation of N-sulfamyl-3-(2-guanidino-thiazol-4-yl-methylthio)-propionamidine (famotidine) of the formula (I)

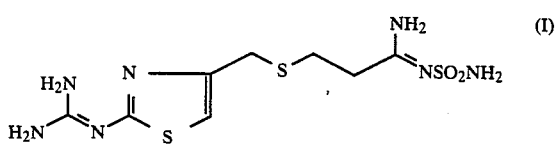

by S-alkylation of 2-guanidino-thiazol-4-yl-methane-thiol obtained from S-(2-guanidino-thiazol-4-yl-methyl)-isothiourea dihydrochloride of the formula (III)

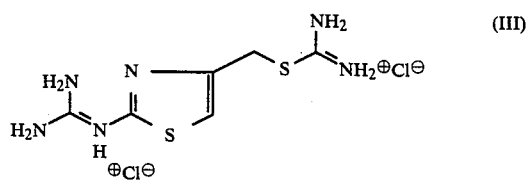

Famotidine is one of the most promising anti-ulcer compounds, inhibiting gastric and intestinal ulceration on the basis of a histamine H2-receptor blocking mechanism. It is about one order of magnitude more potent than cimetidine (Arzneim. Forsch., 32, 734 1982), its daily dose is only 1×40 mg. against the 4×200 mg. daily dose of cimetidine and it has no antiandrogenic activity.

For the preparation of famotidine there are several processes known in the art. A process starting from 3-(2-guanidino-thiazol-4-yl-methylthio)-propionitrile was for example first described in the U.S. Pat. No. 4,283,408 (Yamanouchi). First the imino-methylether hydrochloride of the nitrile was prepared by known chemical methods, which was then converted into the corresponding base, which was obtained as an oily product with a yield of 92.0%. The iminoether base was converted into famotidine by boiling with two equivalents of sulfamide in a methanolic medium and famotidine was isolated by column chromatography, with a yield of 64.4%. The total yield was 59.2%.

The main disadvantage of the process is the isolation by column chromatography, which makes the process practically unsuitable for industrial application. A further drawback is the high consumption of sulfamide (0.9–1.0 kg./kg.).

An inproved method is disclosed in the European Patent Application No. 128,736 of the same company, where the chromatographic purification could be avoided only by preparing and using an iminoether base of substantially higher purity. From 3-(2-guanidino-thiazol-4-yl-methylthio)-propionitrile solid iminoether base was prepared with a yield of 78.8%, which was reacted with 2.2 molar equivalents of sulfamide in a methanolic medium, at 20° to 30° C. for three days. The crude product obtained with a yield of 62% was recrystallized from aqueous dimethyl formamide, and the obtained material was again precipitated with a base, after dissolution in a mixture of water and acetic acid. The total yield for crude famotidine was accordingly merely 48.8%. The main disadvantage of this process is the high consumption of sulfamide, the many and cumbersome steps involved in the process and that it is very time consuming.

According to the U.S. Pat. No. 4,496,737 (Merck) 3-(methylthio)-propionitrile was used as a starting material, which was converted into the corresponding imino-ether base with a yield of 67.2%. The oily product obtained was boiled with 1.5 molar equivalents of sulfamide, for 20 hours. After recovering the excess of sulfamide the product was isolated by column chromatography, with a moderate (26.0%) yield. The N-sulfamyl-3-(methylthio)-propionamide obtained was oxidized into the corresponding sulfoxide with m-chloroperbenzoic acid in a mixture of chloroform and methanol (yield: 83.4%). The sulfoxide compound was then subjected to an elimination reaction by boiling with triethyl amine in an ethanolic medium for 20 to 30 hours. As a result, N-sulfamyl-acrylic amidine of the formula (IV)

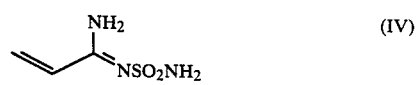

was isolated by column chromatography with a yield of 37.2%.

According to the description, from the S-(2-guanidino-thiazol-4-yl-methyl)-isothiourea dihydrochloride of the formula (III)

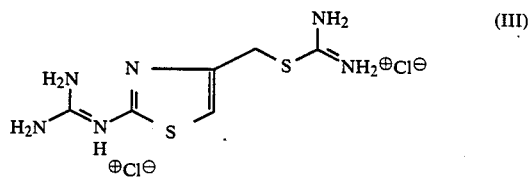

the corresponding mercaptane derivative was then prepared in situ, in aqueous methanol. By reacting the latter compound with N-sulfamyl-acrylamidine of the formula (IV) in a base-catalysed addition reaction, famotidine could be prepared and isolated by means of column chromatography with a yield of 35.6%. A major advantage of this process is that the reactant of the formula (IV) can provide the total side-chain of famotidine, i.e. its reaction with 2-guanidino-thiazol-4-yl-methane-thiol obtained in situ from the isothiuronium salt of the formula (III) yields directly famotidine. This process has, however, several drawbacks, too:

(a) N-sulfamyl-acrylamidine was prepared by a four-step procedure from 3-(methylthio)-propionitrile, with an extremely low (5.5%) yield in several days. The products of the subsequent steps, including famotidine, were isolated by column chromatography.

(b) The yield of the last step resulting in famotidine is rather moderate (35.6%), therefore the specific costs of the process are high.

The purpose of the present invention to provide a new process for the preparation of famotidine, by which it can be prepared with a high yield, in satisfactory purity without any column chromatographic step.

The invention is based on the discovery that 2-guanidino-thiazol-yl-methane-thiol obtained from the compound of the formula (III) in situ may be S-alkylated with a N-sulfamyl-3-halopropionamidine hydrohalide of the formula (II)

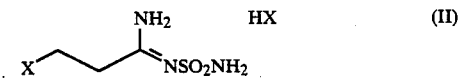 (II)

wherein X is halogen,
very easily in an aqueous alcoholic medium, at room temperature. At the end of the reaction famotidine separates out as a crystalline product, which can be isolated from the sodium chloride dissolved in the aqueous alcoholic medium by filtration.

In our experiments we have surprisingly found that N-sulfamyl-(3-halo)-propionamidine hydrochloride of the formula (II) is an excellent S-alkylating agent. It was first believed that from this reactant in the alkaline aqueous-alcoholic medium N-sulfamyl-acrylamidine of the formula (IV) described in the above-cited patent specification, is formed. According to literature data the alkylations carried out with 3-chloropropionic acid derivatives generally take place through the corresponding acrylic acid derivative, i.e. following an elimination-addition mechanism. The 71% yield we could obtain, which is twice as high as e.g. in the U.S. Pat. No. 4,496,737, and the precipitation of the desired product from the reaction mixture in a pure, crystalline form support the presumption that in our case the S-alkylation proceeds according to a substitution mechanism ($S_N2$). We have further experimentally proved that the elimination of hydrogen chloride from the compound of the formula (II) yields instead of the acrylic acid amidine derivative of the formula (IV) 3-amino-4,5-dihydro-1,2,6-thiadiazine-S,S-dioxide by intramolecular cyclization, which compound does not react with the thiolate formed from the compound of formula (III) in an alkaline medium. It was also highly surprising, particularly in view of the low yields reported in the above patent specification, that the amidine moiety of the N-sulfamyl-(3-halo)-propionamidine remained intact. It is namely well known that amidines are liable to hydrolysis [Houben Weyl-Müller: Methoden der organischen Chemie 8, 703 (1952)].

Accordingly, the invention relates to a new process for the preparation of N-sulfamyl-3-(2-guanidino-thiazol-4-yl-methylthio)-propionamidine of the formula (I)

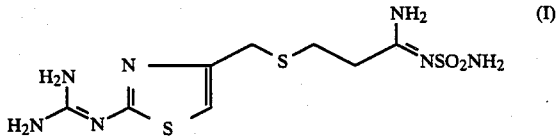 (I)

furtheron referred to as famotidine by S-alkylation of 2-guanidino-thiazol-4-yl-methanethiol obtained in situ from S-(2-guanidino-thiazol-4-yl-methyl)-izothiurea dihydrochloride of the formula (III)

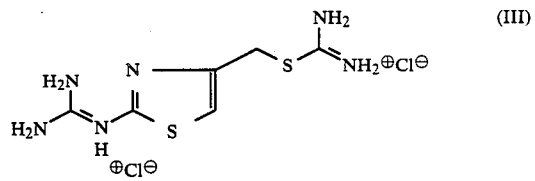 (III)

which comprises carrying our S-alkylation with an N-sulfamyl-3-halopropionamidine of the formula (II)

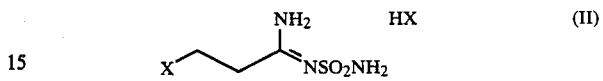 (II)

X is halogen.

The alkylation is preferably carried out in an alkaline aqueous solution. As a base e.g. sodium hydroxide, preferably as a 40% aqueous solution, is employed.

According to a preferred embodiment of the process according to the invention to an aqueous solution of S-(2-guanidino-thiazol-4-yl-methyl)-isothiourea dihydrochloride of the formula (III) and N-sulfamyl-(3-chloro)-propionamide hydrochloride an aqueous-alcoholic sodium hydroxide solution is added dropwise, under stirring. The product (famotidine) precipitated during the reaction is filtered off after cooling the solution, washed with water and then with isopropanol and dried.

The advantages of the process according to the invention may be summed as follows:

(a) The use of N-sulfamyl-acrylamidine of the formula (IV), which can be prepared by a complicated procedure with a very low yield, is avoided.

(b) The end product can be isolated easily, in excellent quality and high purity.

(c) The yields are high (70 to 72%) even on an industrial scale.

The invention will be illustrated in greater detail by the aid of the following non-limiting Example.

EXAMPLE

To a solution of 3.04 g. (0.01 mole) of S-(2-guanidino-thiazol-4-yl-methyl)-isothiourea dihydrochloride and 2.22 g. (0.01 mole) of N-sulfamyl-(3-chloro)-propionamidine hydrochloride in 8.0 ml of deionized water a mixture of 4.0 ml of a 10N sodium hydroxide solution (0.04 mole) and 6.0 ml ethanol is added dropwise, at 25° to 30° C., under stirring. The homogeneous mixture obtained (pH 11), is stirred for further one and a half hours and cooled with ice water for one hour. The product is filtered off, washed twice with deionized water and twice with isopropanol and dried until reaching an steady weight.

2.40 g (71.2%) of famotidine are obtained.

Melting point: (159°)-160° to 162° C. decomposition at 165° C.

IR spectrum (KBr): $NH_2$ 3506, 3452, 3400; NH 3360, 3377, 3240; C=N 1639; C=N (conj.) 1604 br; $SO_2$ 1288, 1145 $cm^{-1}$ Protone NMR spectrum (DMSO $d_6$): S— $CH_2$— $CH_2$— N: 2.6 ppm multiplette; Ar— $CH_2$— S: 3.6 ppm singulette; Ar— H: 6.5 ppm singulette; NH, $NH_2$: 3.5; 6.8; 7.4; 8.3 ppm, br, exchangeable.

The starting materials at the Formula (II) are prepared by reacting a compound of the Formula (V)

wherein X is as defined above,
with sulfamide of the formula (VI)

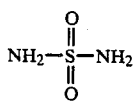

in the presence of a hydrogen halide.

According to a preferred method a 3-halopropionitrile is prepared in situ from acrylonitrile by addition with a hydrogen halide (e.g. with gaseous hydrogen chloride or hydrogen bromide).

The starting materials of the Formula (II) can for example be prepared by introducing dry hydrogen chloride gas into a stirred solution of the sulfamide in an excess of 3-chloropropionitrile (or acrylonitrile). The precipitated crystalline compound of the Formula (II) is filtered off upon cooling and optionally after dilution with an organic solvent, washed with acetone and dried.

Favorable results are obtained by reacting 1 mole of a sulfamide with 1.5 to 8 moles, preferably 1.8 to 2.5 moles, of a 3-halopropionitrile derivative of the Formula (V), at 10° C. to 100° C., preferably 10° C. to 60° C., for 1 to 100, preferably 20 to 60 hours, while a hydrogen halide is passed through the solution. Solvents, e.g. ethers, may be used.

PREPARATION EXAMPLE 1

N-Sulfamyl-3-chloropropionamidine hydrochloride

To a suspension of 9.61 g. (0.10 moles) of sulfamide in 60 ml (68 g., 0.76 mole) of 3-chloropropionitrile dry hydrogen chloride gas is introduced under stirring at 50° to 60° C. for 5 hours. The gain in weight is about 9 to 12 g. The reaction mixture is then cooled with ice water for one hour, the product is filter off, washed twice with acetone and dried up to steady weight.

Yield: 14.9 g. (67.1%)
Melting point: (142°)-144°-146° C. decomp.)
Analysis:
Calculated: C 16.24%, H 4.08%, Cl 31.90%, N 18.92%;
Found: C 16.30%, H 4.13%, Cl 31.86%, N 18.90%.
Purity: 97.0% (determined by potentiometric titration in a methanolic medium)
IR spectrum (in KBr tablet, determined on a "Perkin-Elmer 257" equipment): C≡N: 1675 cm$^{-1}$, SO$_2$: 1170 cm$^{-1}$ br, C—Cl: 660 cm$^{-1}$.
Protone NMR spectrum (d$_6$-DMSO/D$_2$O, determined on a "Varian EM 360" equipment): =C—CH$_2$—: 3.05 ppm, t; Cl—CH$_2$—: 4.00 ppm, t; X—H: 8.5 ppm, S(b)*.

PREPARATION EXAMPLE 2

N-Sulfamyl-3-chloropropionamidine hydrochloride

To a stirred suspension of 9.61 g. (0.10 mole) of sulfamide in 30 ml (34 g., 0.38 mole) of 3-chloropropionitrile hydrogen chloride gas is introduced, as described in Example 1. After cooling with ice water for one hour the reaction mixture is diluted with 30 ml of dry ethyl ether, the product is filtered off, washed twice with acetone and dried.

Yield: 16.15 g. (72.7%)
Melting point: (142°)-144°-146° C. (decomp.).

PREPARATION EXAMPLE 3

N-Sulfamyl-3-chloropropionamidine hydrochloride 18 to 20 g. of hydrogen chloride gas are absorbed in a stirred suspension of 9.61 g. sulfamide in 27 g. (34 ml, 0.5 mole) of acrylonitrile at 0° to +2° C. The reaction mixture is then heated up to 50° C. and hydrogen chloride gas is passed through it for three hours, while the inner temperature is kept between 50° C. and 60° C. The thick, white crystal suspension obtained is cooled to room temperature, diluted with 25 ml of isopropyl ether, cooled with ice water, filtered, washed with acetone and dried.

Yield: 16.0 g. (72.0%)
Melting point: (143°)-145°-147° C. (decomp.).

PREPARATION EXAMPLE 4

N-Sulfamyl-3-chloropropionamidine hydrochloride

A suspension of 9.61 g. of sulfamide with 26.9 g. (24.0 ml, 0.30 mole) of regenerated 3-chloropropionitrile and 10.7 g. (23. ml, 0.2 mole) of acrylonitrile is stirred continuously whereupon 7 to 8 g. of hydrogen chloride gas are absorbed in the suspension at a temperature of 0. to +2° C. The mixture is then heated up to 50° C., and hydrogen chloride gas is passed through it for further 3 hours, at a temperature of 50° C. to 60° C. After dilution with 25 ml of isopropyl ether and cooling with ice the product obtained is filtered off, washed with acetone and dried.

Yield: 15.5 g. (69.8%)
Melting point: (143°)-144°-146° C. (decomp.).

We claim:

1. Process for the preparation of N-sulfamyl-3-(2-guanidino-thiazol-4-yl-methylthio)-propionamidine of the formula (I)

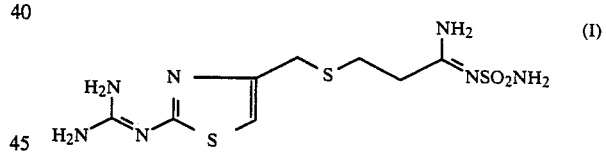

(famotidine) by S-alkylation of 2-guanidino-thiazol-4-yl-methanethiol obtained from S-(2-guanidino-thiazol-4-yl-methyl)-isothiourea dihydrochloride of the formula (III)

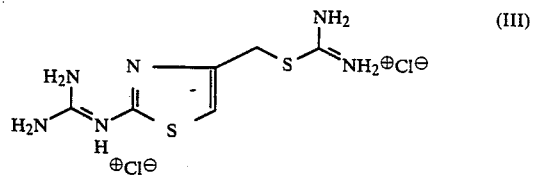

by in situ treatment with a base, which comprises carrying out S-alkylation with a N-sulfamyl-3-halopropionamidine of the formula (II)

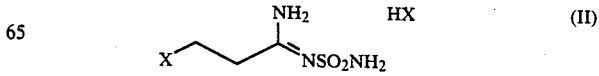

wherein X stands for halogen.

2. A process as claimed in claim 1, in which alkylation is carried out in an alkaline mixture of water and an alkanol having from 1 to 4 carbon atoms.

3. A process as claimed in claim 1 which comprises using sodium hydroxide as a base.

4. A process as claimed in claim 4, in which sodium hydroxide is employed as a 40% aqueous solution.

5. A process as claimed in claim 3 in which the base is added to the reaction mixture at a temperature of 0° to 50° C.

6. A process as claimed in claim 5 in which the base is added to the reaction mixture at a temperature of 20° to 30° C.

* * * * *